United States Patent
Feigenwinter et al.

(10) Patent No.: US 9,433,455 B2
(45) Date of Patent: Sep. 6, 2016

(54) FRACTURE FRAGMENT MOBILITY TESTING FOR VERTEBRAL BODY PROCEDURES

(75) Inventors: Gregor Feigenwinter, Lampendberg (CH); Jacques Teisen, Zurich (CH)

(73) Assignee: DePuy Synthes Products, Inc., Raynham, MA (US)

( * ) Notice: Subject to any disclaimer, the term of this patent is extended or adjusted under 35 U.S.C. 154(b) by 1324 days.

(21) Appl. No.: 12/970,486

(22) Filed: Dec. 16, 2010

(65) Prior Publication Data

US 2012/0157832 A1 Jun. 21, 2012

(51) Int. Cl.
  *A61B 5/05* (2006.01)
  *A61B 17/88* (2006.01)
  *A61B 6/00* (2006.01)

(52) U.S. Cl.
  CPC ............ *A61B 17/8855* (2013.01); *A61B 6/505* (2013.01)

(58) Field of Classification Search
  CPC ............ A61B 8/00; A61B 5/05; A61B 8/08
  USPC .................... 600/407, 431, 587, 432; 606/94
  See application file for complete search history.

(56) References Cited

U.S. PATENT DOCUMENTS

| | | |
|---|---|---|
| 7,166,121 B2 | 1/2007 | Reiley et al. |
| 8,518,115 B2 | 8/2013 | Chavatte et al. |
| 2003/0088249 A1 | 5/2003 | Fürderer |
| 2003/0220649 A1 | 11/2003 | Bao et al. |
| 2005/0090852 A1 | 4/2005 | Layne et al. |
| 2007/0010848 A1 | 1/2007 | Leung et al. |
| 2007/0049849 A1* | 3/2007 | Schwardt et al. ............ 600/587 |
| 2007/0219445 A1* | 9/2007 | Liebschner et al. .......... 600/431 |
| 2009/0069850 A1 | 3/2009 | Feurderer |
| 2011/0028981 A1* | 2/2011 | McKay ......................... 606/102 |
| 2011/0224675 A1* | 9/2011 | Tofighi et al. .................. 606/94 |

OTHER PUBLICATIONS

Fürderer, S., et al., "Vertebral body stenting," Orthopäde, vol. 31, 2002, pp. 356-361.
Magerl, F., et al., "A comprehensive classification of thoracic and lumbar injuries," European Spine Journal, vol. 3, 1994, pp. 184-201.

* cited by examiner

*Primary Examiner* — Joel Lamprecht
(74) *Attorney, Agent, or Firm* — Meunier Carlin & Curfman LLC

(57) ABSTRACT

A fracture mobility testing system is provided for use in surgical procedures for augmenting vertebral bodies having collapsed due to compression fractures. The testing system is utilized to determine if the cortical shell of the vertebral body has begun to heal over the fracture lines to the point at which height restoration is not possible. Depending on the feedback provided by the testing system, the surgeon may elect to proceed with any of a variety of known height restoration techniques if the fractured portions of the vertebral body are still mobile, or may elect for a simple vertebroplasty procedure without height restoration if the feedback from the testing system determines that the cortical outer portions of the fractured vertebral body have fused to one another to the point at which height restoration is no longer an option.

8 Claims, 4 Drawing Sheets

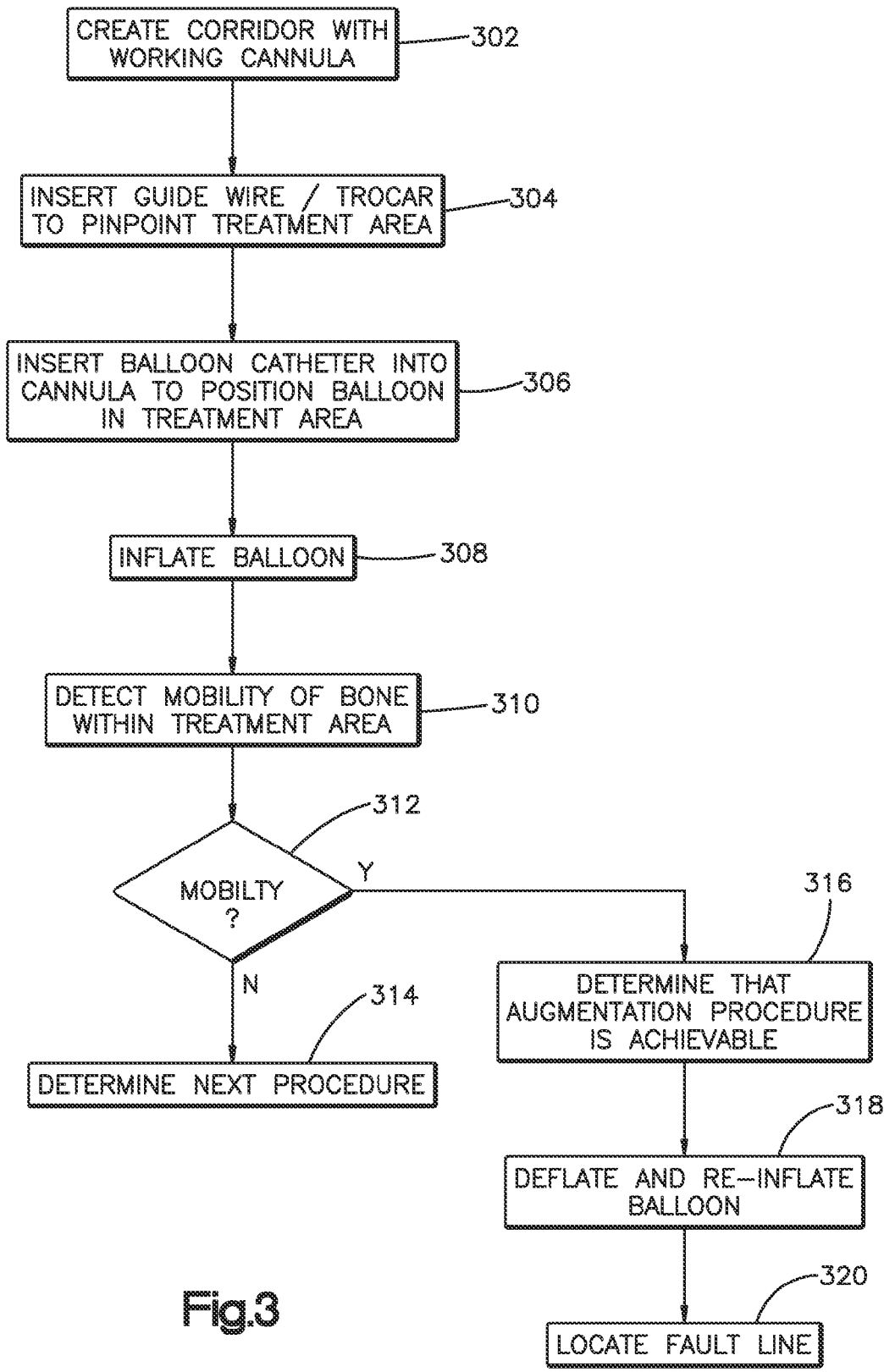

FRACTURE FRAGMENT MOBILITY TESTING FOR VERTEBRAL BODY PROCEDURES

BACKGROUND

Vertebral compression fractures, as illustrated in FIG. 1, represent a generally common spinal injury and may result in prolonged disability. F. Margerl et al: A comprehensive classification of thoracic and lumbar injuries, Eur Spine J 184-201, 1994. These fractures involve collapsing of one or more vertebral bodies 25 in the spine. Compression fractures of the spine usually occur in the lower vertebrae of the thoracic spine or the upper vertebra of the lumbar spine. They generally involve fracture of the anterior portion of the affected vertebra 25 (as opposed to the posterior side). Spinal compression fractures can result in increased kyphotic deformation of the normal alignment or curvature of vertebral bodies in the affected area of the spine. Spinal compression fractures and/or related spinal deformities can result, for example, from metastatic diseases of the spine, from trauma or can be associated with osteoporosis.

Several minimally invasive surgical (MIS) procedures for treating vertebral compression fractures have been developed and tested with various degrees of success. These procedures generally involve the use of a cannula or other access tool inserted into the posterior of the effected vertebral body through the pedicles. The most basic of these procedures is vertebroplasty, which literally means fixing the vertebral body, and may be done with or without first repositioning the bone to restore the original height of the collapsed vertebral body.

In such MIS procedures, a cannula or special bone needle is typically passed through the soft tissues of the back. X-ray image guidance may allow the position of the needle to be seen at all times. Once the need is positioned, a small amount of polymethylmethacrylate (PMMA) or other appropriate orthopedic cement is pushed through the needle into the vertebral body. PMMA, the most common material used today, is a medical grade substance that has been used for many years in a variety of orthopedic procedures. Generally, the cement is mixed with an antibiotic to reduce the risk of infection, and a radiopaque powder containing barium sulfate, zirconium oxide or tantalum to allow it to be seen on X-ray.

Vertebroplasty is a treatment for vertebral compression, which can be effective in the treatment of fracture pain, the prevention of further collapse, and a return to mobility in patients. However, height restoration is an optional step of this procedure and thus, spinal deformity might not be addressed. Another treatment is balloon kyphoplasty, in which a catheter having an expandable balloon tip is inserted through a cannula, sheath or other introducer into a central portion of a fractured vertebral body. Kyphoplasty, by expanding the balloon in situ within the vertebral body, may potentially achieve the reconstruction of the appropriate lordosis, or normal curvature of the spine. The balloon is removed, leaving a void within the vertebral body, and PMMA or other filler material is then injected through the cannula into the void as described above with respect to vertebroplasty. The cannula is removed and the cement cures to fill or fix the bone. One potential disadvantage with this procedure is that when the balloon is removed the vertebral body may return to its collapsed position.

Another approach for treating vertebral compression fractures is a mesh-based system that provides material delivery using an expandable mesh graft balloon, or containment device, within the involved vertebral body. The balloon graft remains inside the vertebral body after its inflation, which reduces the chance of resettling, such as can occur during a kyphoplasty procedure when the balloon is withdrawn.

Still another procedure used in the treatment of vertebral compression fractures is an expandable polymeric slotted tube mass known as a Sky Bone Expander. This device can be expanded by compressing said tube longitudinally, increasing the slotted tube's diameter, but like kyphoplasty, once vertebral height is restored, the Sky Bone Expander is removed allowing for possible settling prior to cement injection and curing.

A proposed improved procedure for repositioning and augmenting vertebral body compression fractures is vertebral body stenting, for example as described in Furderer et al., "Vertebral body stenting", Orthopade 31:356-361, 2002; European Patent number EP1308134B1; and United States Patent Application publication numbers US2003/0088249 and/or US2009/0069850, each of which is incorporated by reference herein in its entirety. Vertebral body stenting generally involves inserting into a vertebral body a balloon-tipped catheter surrounded by a stent. After insertion of the balloon and stent, the balloon is inflated, e.g., using fluid pressure, thereby expanding the stent within the vertebral body. After expansion of the stent, the balloon may be deflated and removed, with the stent remaining inside the vertebral body in an expanded state, defining a cavity to be filled with bone cement.

Another proposed improved procedure for repositioning and augmenting vertebral body compression fractures is the implementation of a porous or permeable containment device, as is described in PCT application WO2009064847, the contents of which are incorporated herein in their entirety. The porous containment device is inserted into the interior volume of a targeted vertebral body for restoring the anatomy of the bone, and is expandable by filling with, for example, a bone filler material. The containment device preferably permits the bone filler material to flow out of the containment device through one or more pores or flow-directing tentacles such that the bone filler material interdigitates with the surrounding bone tissue. The porous containment device is then de-docked from its insertion catheter and remains within the interior of the vertebral body.

While the concepts of vertebral body stenting and porous containment vertebral augmentation provide promise over other known methods for treating compression fractures, there remains a need for improved methods for repositioning, restoring height, and augmenting fractured vertebral bodies in any of the above-mentioned vertebral body augmentation procedures and potentially other bone augmentation procedures. One of the main goals of vertebral body augmentation procedures is the restoration of height to the collapsed vertebral body; however, such height restoration can only be achieved if the fractured portions of the vertebral body are mobile with respect to one another, as during the healing process hard bone, comparable to the compact cortical shell of the vertebral body, begins to fuse about and over the fractured region, especially in fast-healing younger patients whose injuries are the result of trauma (as opposed to severely osteoporotic elderly patients). Once the fractured portions of the vertebral body begin to fuse to one another in a collapsed configuration, height restoration may be impossible to achieve without resorting to more invasive means (e.g., osteotomy in which the fused bone is cut to provide bone fragment mobility again).

As can be appreciated, there is a wide variety of potential procedures as well as a wide variety of potential bone conditions; and each bone condition will not respond the same to the various procedures.

SUMMARY

The present disclosure relates generally to orthopedics. More specifically, it relates to fracture mobility testing of, e.g., a vertebral body. A fracture mobility testing system is provided for use in surgical procedures for augmenting vertebral bodies having collapsed due to compression or burst fractures. The testing system is utilized to determine if hard bone has begun to heal over the fracture lines of the vertebral body to the point at which height restoration is not possible. Depending on the feedback provided by the testing system, the surgeon may elect to proceed with any of a variety of known height restoration techniques if the fractured portions of the vertebral body are still mobile, or may elect direct cement augmentation without height restoration if the feedback from the testing system determines that the cortical outer portions of the fractured vertebral body have fused to one another to the point at which height restoration is no longer an option.

In accordance with some implementations, there is a method for diagnostic testing of a treatment area for receiving a non-fluid implant, i.e. an implant that is already solid during its implantation, but can be expanded in-situ from an initial to a final geometric configuration. The method may include inserting an expandable balloon into the treatment area; inflating the expandable balloon within the treatment area; determining mobility characteristics of bone within the treatment area; deflating the expandable balloon; and performing a subsequent procedure to insert and deploy the non-fluid implant within the treatment area.

In accordance with some implementations, there is a method for diagnostic testing of mobility of a fracture of a vertebral body. The method may include creating an access corridor to a treatment area of the vertebral body by performing a sequence of cannula-trocar-drill-plunger access steps; inserting a catheter into the cannula having an expandable balloon into the treatment area; inflating the expandable balloon within the treatment area; determining if endplates associated with the fracture of the vertebral body have moved with respect to each other; and deflating the expandable balloon.

In accordance with yet other implementations, there is a method for determining fracture mobility. The method may include preparing an expandable balloon for insertion into a bone; determining an amount of fracture collapse of the bone; inserting the expandable balloon into the bone; inflating the balloon with a solution having radiopaque properties; determining an amount of fracture height restoration of the bone with the balloon inflated; deflating the balloon; determining an amount of fracture height restoration after the balloon has deflated; and determining a procedure repair based on at least one of the amount of fracture height restoration of the bone with the balloon inflated and the amount of fracture height restoration after the balloon has deflated.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

The foregoing summary, as well as the following detailed description of preferred embodiments, will be better understood when read in conjunction with the appended drawings. For the purposes of illustrating the preferred embodiments, there is shown various drawings. It should be understood, however, that the application is not limited to the precise arrangements and instrumentalities shown herein. In the drawings:

FIG. 3 illustrates an example operational flow chart of processes performed for testing fracture mobility of a collapsed vertebral body;

DETAILED DESCRIPTION

Figure 1:
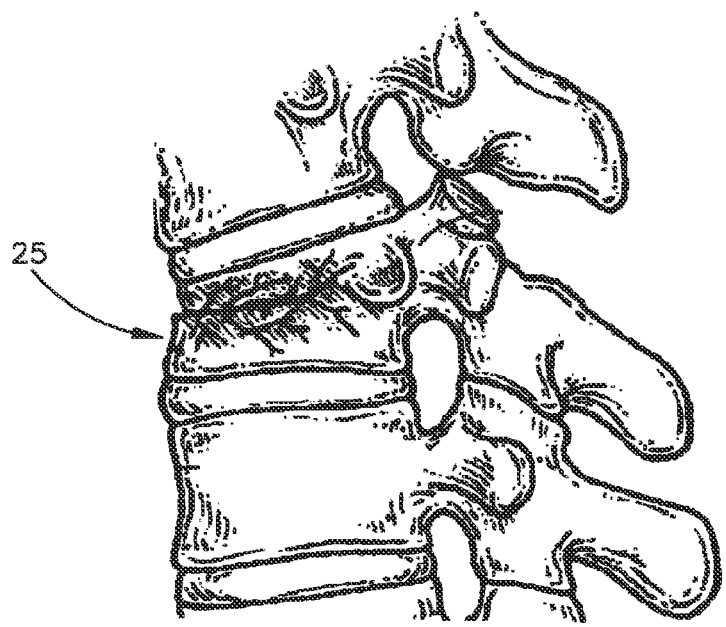
FIG. 1 illustrates a lateral plan view of a human spine with a vertebral compression fracture.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the geometric center of the fracture mobility testing system and related parts thereof. The words, "anterior", "posterior", "superior," "inferior" and related words and/or phrases designate preferred positions and orientations in the human body to which reference is made and are not meant to be limiting. The terminology includes the above-listed words, derivatives thereof and words of similar import.

Figure 2:
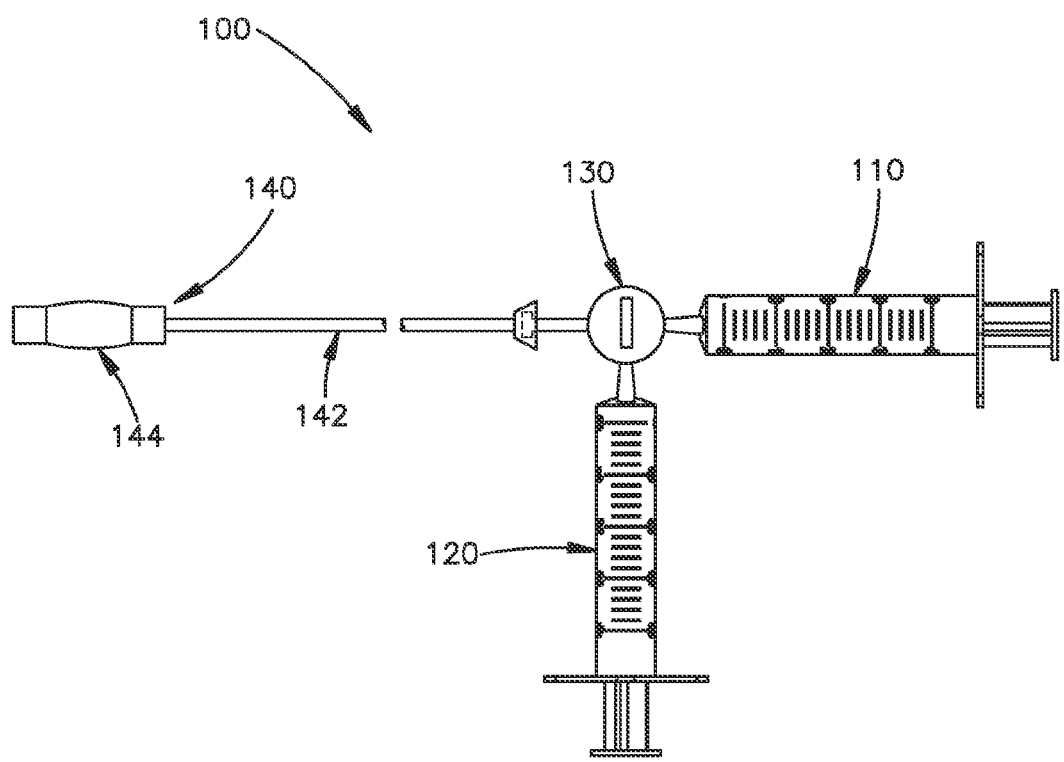
FIG. 2 illustrates a side plan view of a fracture mobility testing system in accordance with a first embodiment of the present invention.

Referring to FIGS. 2-3, a fracture mobility testing system 100 is provided that includes a first syringe 110, a second syringe 120, a three-way stop-cock coupling unit 130, and a balloon catheter 140, the balloon catheter 140 further including a shaft 142, the distal end of which terminates in a balloon 144. The three-way stopcock coupling 130 provides a selective coupling for fluid or gas communication between the balloon catheter 140 and the first and second syringes 110, 120. FIGS. 2-3 further include a working cannula 150 that provides an access corridor to the interior of a vertebral body. The first syringe is configured for inflating or expanding the balloon while the second syringe is configured for creating a vacuum within the balloon catheter 140.

In some implementations, the first syringe and/or the second syringe may be replaced with a pressure syringe, such as the Vertebral Body Stenting (VBS) Inflation System, available from Synthes. The VBS Inflation System may be connected to the three-way stopcock coupling unit 130 to pressurize the balloon 144 or to create a vacuum within the interior of the fracture mobility testing system 100. In a first embodiment, the balloon 144 is a non-elastic balloon but, in alternate embodiments, may be elastic. The balloon 144 may be essentially spherical or elliptical or may assume a range of alternate geometries that are well-configured for imparting a distraction force to the vertebral endplates, and may include flattened superior and inferior surfaces.

Balloon 144 may be designed to have particular properties that are beneficial to diagnosing fracture mobility. For example, balloon 144 may be designed to withstand high pressures and large volume increases thereby providing for height restoration, as opposed to conventional curette type cavity creation devices that provide no height restoration. In addition, balloon 144 may have an expansion ratio (beginning diameter/ending diameter) much greater than that provided by a curette. Balloon 144 may also expand while keeping a large surface contact 360° around the circumference (increasing with continued inflation) versus the point contact of a curette (which must be rotated and longitudinally shifted to reliably and completely check for 360° all-round fixation mobility). Further, balloon 144 may be designed to create a larger volume than a volume-constant tipped curette (<200%), resulting in a larger and more radiopaque body.

Figure 4A:
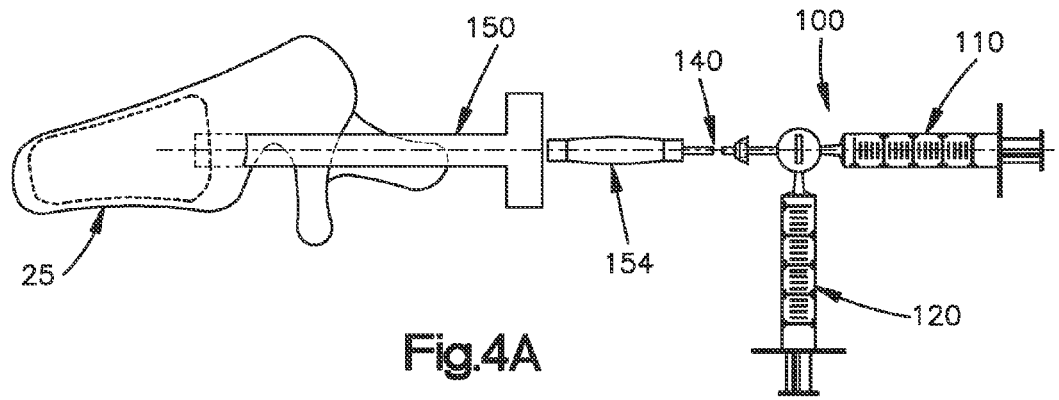
FIGS. 4A-4C illustrate a side plan view of the fracture mobility testing system of FIG. 2 being utilized in a method for testing fracture mobility of a collapsed vertebral body of FIG. 3.
Figure 4B:
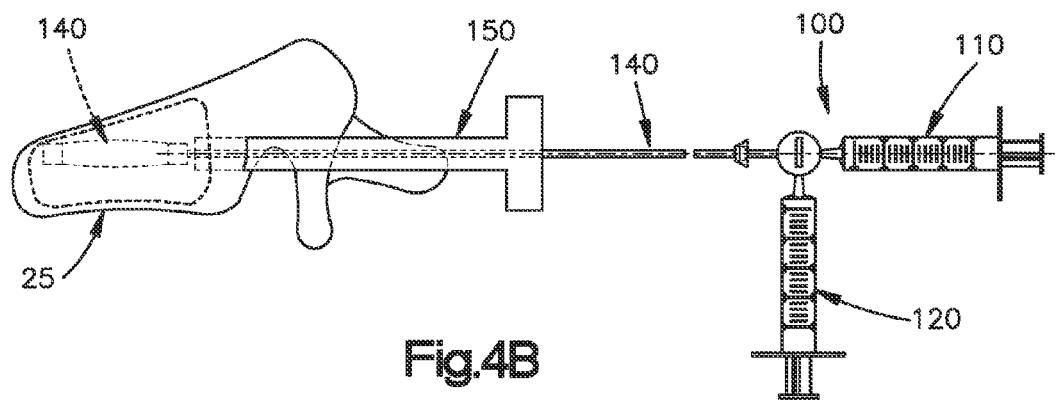
Figure 4C:
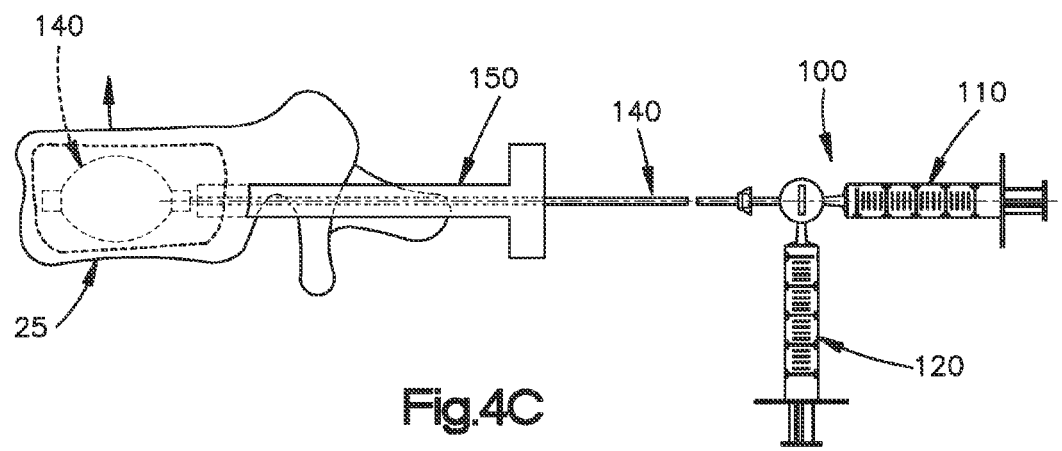
Figure 5:
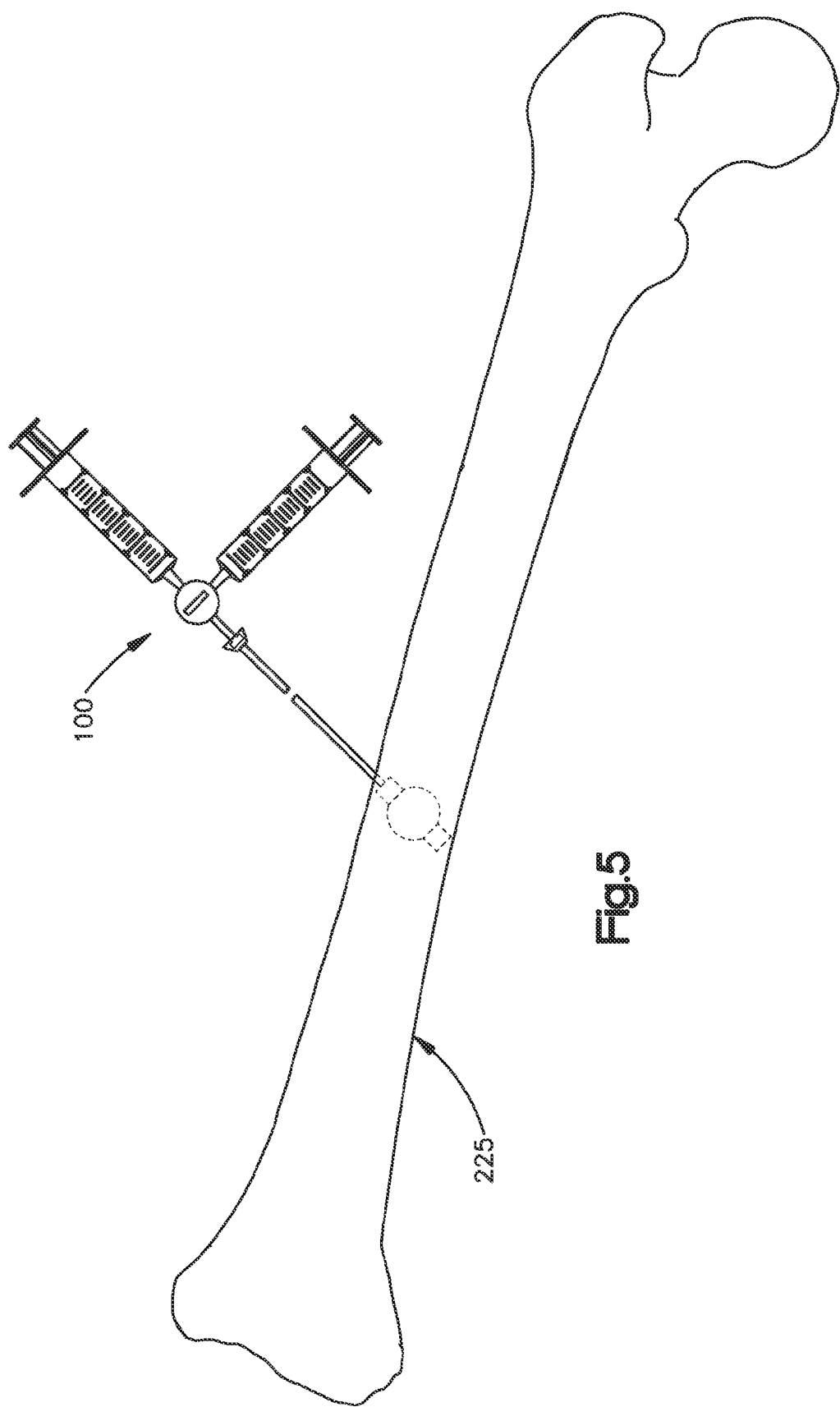
FIG. 5 illustrates a side plan view of the fracture mobility testing system of FIG. 2 being utilized in an alternate method for testing fracture mobility of a fractured long bone in accordance with a second embodiment of the present invention.

In operation, and in continuing reference to FIGS. 2-4, a transpedicular access corridor is created using the working cannula 150 (block 302). In a first embodiment, the procedure begins by placing the patient in a prone position. If a general anesthesia is used, the patient can be placed in hyperextension. The surgical field of interest is then checked with a C-arm to ensure free access for the C-arm in the A-P and lateral directions at the level of pathology. The area to be treated is then draped and cleaned. The vertebral body 25 to be augmented is then identified using the C-arm, which is adjusted exactly in the AP projection so that the view is parallel to the endplates and in order that the pedicles appear symmetric. A second C-arm may be used in order to obtain a bi-planar projection and gain control of both planes simultaneously. Otherwise, the C-arm can be switched into the other projection when necessary. With the C-arm installed in the AP projection, the incision site is planned. The C-arm is then used to localize a stab incision into the skin.

A guide wire is then pushed through the soft tissue until the bony surface of the spine is touched, while the C-arm is used for controlled placement (block 304). A wire holder can be used in order to avoid radiation exposure to the surgeon's fingers. The orientation of the guide wire is then made with the C-arm in the AP view. Once the bony surface is touched, the tip of the guidewire is positioned lateral of the eye of the pedicle at its upper third. At the thoracic spine, the guide wire is made to sit on the costo-transverse process and at the lumbar spine, the guide wire is made to sit in the edge of the lateral facet and the transverse process. The guide wire is then advanced convergent in the projection of the pedicle. Guide wires are then preliminarily inserted at all levels where cement augmentation is planned, with each vertebrae's position stored in the image intensifier of the C-arm display. The working cannula 150 is then placed over the guidewire and the guidewire is removed.

A vacuum is drawn within the interior of the fracture mobility testing system 100 by manipulating the stop cock 130 into a position configured for enabling the second syringe 120 to create or maintain a vacuum within the interior of the balloon catheter 140 by manipulating the plunger with respect to the second syringe 120. The fracture mobility testing system 100 is then utilized by inserting the balloon catheter 140 through the working cannula 150 such that the balloon 144 is placed into the interior of the vertebral body 25 (block 306). With the C-arm in a lateral or A-P position (or both, if two C-arms are being utilized), the balloon 144 is then filled (e.g., with saline solution, other biocompatible material, contrast agents, combinations thereof, etc.) by manipulating the stop cock 130 into a position configured to enable fluid communication between the contents of the first syringe 110 and the interior of the balloon catheter 140 and plunging the contents of the first (injection) syringe 110 through the balloon catheter 140 and into the interior of the balloon 144, thereby causing the balloon 144 to expand in volume (block 308).

Mobility of the vertebral body 25 may now be detected (block 310). For example, because no cavity has been created within the interior of the vertebral body 25, expansion of the balloon 144 will either force one or more of the vertebral body endplates to distract from one another. This may be the case when the cortical surfaces of the vertebral body 25 have not fused to one another over the fracture lines of the collapsed vertebral body 25 (block 312: YES). In such a case, cement augmentation and height restoration of the collapsed vertebral body 25 is achievable using any of a variety of subsequent augmentation steps known in the art and as described in the background section (block 316). In the case in which the mobility of the fractured portions of the vertebral body has been confirmed, the surgeon may elect to deflate and re-inflate the balloon 144 several times after adjusting slightly the position of the balloon (block 318). This may be performed to determine where the fault line(s) or hot spot(s) for optimal balloon expansion and cancellous bone compression are located in the fractured vertebral body 25 to better plan the next steps of the procedure (block 320).

However, when the cortical bone surfaces or cancellous bone portions of a collapsed vertebral body 25 have begun to fuse to one another over the fracture lines, the increasing volume and pressure of the expanding balloon 144 will not be sufficient to force the one or more endplates of the collapsed vertebral body 25 to become displaced with respect to one another (block 312: NO). Any mobility or lack thereof can easily be perceived by the surgeon by viewing the C-arm images during the injection of contrast agent to expand the volume of the balloon 144. In the case in which the fracture mobility step has proven that there is no mobility to the fractured portions, the surgeon may elect to perform a simple kyphoplasty, in which cement is injected inside the cavity defined by the access corridor using known techniques through the working cannula 150 without achieving height restoration of the vertebral body, but such that the boney structure is prevented from further collapse and stabilized as is (block 314).

Alternately, the surgeon may decide to attempt to manually distract the endplates of the collapsed vertebral body 25 using instruments such as curettes or other more resilient cavity creation tools. Such a decision may be based upon the age and health and pathology of the patient, as the height of an elderly and osteoporotic patient's recently collapsed vertebral body may be more readily restored than a young, relatively healthy individual who underwent trauma such as a car accident and whose treatment was neglected for some time, allowing the cortical surfaces of his collapsed vertebral body to begin to heal and fuse over the fracture lines.

In an alternate embodiment, an extrapedicular approach may be utilized instead of the transpedicular approach described above. A bipedicular procedure, in which two balloon catheters 140 are inserted, one through each pedicle, may be utilized. The same balloon catheter 140 can further be sequentially utilized through each of the bipedicular access corridors and into the interior of the vertebral body 25 and inflated, deflated, and removed.

In the transpedicular and extrapedicular approaches described above, the guide wire or trocar may be initially inserted into a treatment area until they reach a treatment area of the vertebral body. The working cannula 150 may positioned over the guide wire or trocar to for insertion and proper positioning of the balloon catheter 140. In some embodiments, the fracture mobility testing system 100 may further include sensing elements for determining the volume and/or pressure within the interior or the pressure upon the exterior of the balloon 144. Such a volume and/or pressure sensing element may sense the force applied to the plunger of the first and/or second syringes 110, 120.

In an alternate embodiment, and in reference to FIG. 4, the fracture mobility testing system 100 is configured, with or without minor modifications, for use in testing the mobility and healing status of long bone fractures as well, to assist in preoperative planning for the reduction of the long bone fracture.

It will be appreciated by those skilled in the art that changes could be made to the preferred embodiment described above without departing from the broad inventive concept thereof. It is understood, therefore, that this invention is not limited to the particular embodiment disclosed, but it is intended to cover modifications within the spirit and scope of the present invention as defined by the present description.

What is claimed:

1. A method for diagnostic testing of a treatment area for receiving a non-fluid implant, comprising:
   inserting an expandable balloon into the treatment area;
   capturing a first image of at least one of the treatment area and the expandable balloon and displaying the first image;
   inflating the expandable balloon within the treatment area;
   capturing a second image of at least one of the treatment area and the expandable balloon while inflating the expandable balloon and displaying the second image;
   comparing the first and second images of at least one of the treatment area and the expandable balloon to determine a difference in position of a bone located in the treatment area to determine the mobility of bone within the treatment area in response to inflation of the expandable balloon;
   deflating the expandable balloon; and
   performing a subsequent procedure to insert the non-fluid implant within the treatment area.

2. The method of claim 1, further comprising:
   injecting a contrast agent within the expandable balloon; and
   capturing an image of the injected contrast agent and displaying the image; and
   comparing the image with at least one of the first and second images to determine a difference in position of at least one of the contrast agent and the bone to determine the mobility of the bone in the treatment area in accordance with a size or shape of the expandable balloon after injecting the contrast agent.

3. The method of claim 2, wherein the treatment area is a vertebral body and determining the mobility of the bone in the treatment area comprises determining the mobility of a fractured portion of the vertebral body.

4. The method of claim 3, further comprising:
   adjusting a position of the expandable balloon within the treatment area; and
   re-inflating the expandable balloon to determine where a fault line is located on the fractured bone in the treatment area.

5. The method of claim 1, further comprising:
   determining that a fracture of the bone is immobile; and
   performing the subsequent procedure by injecting cement into the cavity defined by the access corridor within the treatment area, without moving bone.

6. The method of claim 1, further comprising:
   wherein when the bone within the treatment area is determined to be mobile, creating a cavity within an interior of the fractured bone.

7. The method of claim 1, wherein mobility of the bone within the treatment area is correlated to at least one of mobility of a fracture of the bone, compressibility of an interior of the bone, a presence of sclerotic bone areas within the interior of the bone, and a presence of hardened bone due to tumors.

8. The method of claim 1, further comprising:
   sensing at least one of a volume and pressure of an inflatable medium used during inflation of the expandable balloon within the treatment area;
   tracking a change in the at least one of a volume and pressure data to determine a difference the mobility of bone within the treatment area in response to inflation of the expandable balloon.

* * * * *